United States Patent [19]

McClure

[11] Patent Number: 4,601,885
[45] Date of Patent: Jul. 22, 1986

[54] STERILIZATION SYSTEM
[75] Inventor: Harry A. McClure, Carversville, Pa.
[73] Assignee: Adtech, Inc., Lansdale, Pa.
[21] Appl. No.: 385,500
[22] Filed: Jun. 7, 1982
[51] Int. Cl.[4] ............ F16K 31/02; G05D 7/06; G05B 19/00; A61L 2/06
[52] U.S. Cl. .................... 422/114; 137/599; 141/86; 141/90; 422/115; 422/116; 422/295
[58] Field of Search ............ 422/26, 115, 114, 297, 422/295, 116; 222/148, 443; 137/241, 625.28, 625.29, 624.11, 599; 141/85, 86, 88, 89, 90, 91, 92, 183, 243; 53/425, 426, 167, 551; 134/22.11, 22.15; 123/480, 585, 589

[56] References Cited
U.S. PATENT DOCUMENTS

| | | | |
|---|---|---|---|
| 2,210,017 | 8/1940 | Wetherby-Williams et al. | 53/426 |
| 2,603,834 | 7/1952 | Ramsey | 422/116 |
| 3,716,083 | 2/1973 | Tuna et al. | 53/167 X |
| 3,826,612 | 7/1974 | Black | 422/116 X |
| 3,911,642 | 10/1975 | Ernstsson et al. | 53/426 |
| 3,912,535 | 10/1975 | Rausén | 141/90 X |
| 3,964,526 | 6/1976 | Sindermann | 222/148 X |
| 3,970,426 | 7/1976 | Stark et al. | 422/306 X |
| 3,994,686 | 11/1976 | Rauser et al. | 53/167 |
| 4,114,578 | 9/1978 | Hattori et al. | 123/589 |
| 4,146,000 | 3/1979 | Hattori et al. | 123/589 X |
| 4,171,604 | 10/1979 | Weikert | 53/167 X |
| 4,213,795 | 7/1980 | Ernstsson et al. | 141/90 X |
| 4,216,185 | 8/1980 | Hopkins | 422/116 X |
| 4,218,265 | 8/1980 | Fuchs et al. | 53/167 X |
| 4,287,909 | 9/1981 | Thompson et al. | 137/599 X |
| 4,287,911 | 9/1981 | Houdeshell | 137/599 X |
| 4,353,398 | 10/1982 | Weiler et al. | 141/85 X |
| 4,374,785 | 2/1983 | Wyatt | 137/599 X |
| 4,396,044 | 8/1983 | Ahlers | 141/90 |

Primary Examiner—Barry S. Richman
Assistant Examiner—B. Heaney
Attorney, Agent, or Firm—Walter B. Udell

[57] ABSTRACT

A steam sterilization system for a fitting machine having dispensing nozzles connected to a source of product supply, the sterilizing system including a novel autoclave apparatus and a novel condensate purge system. The autoclave structure causes sterilizing steam to flow downward through the inside of the dispensing nozzle to its open ended bottom where it reverses and flows upward between the inside face of a reversing tube and the outside face of the dispensing nozzle to a series of holes through the sidewall of the reversing tube where it emerges and goes down between the outside face of the reversing tube and the inside face of the autoclave shell thereafter passing down into a steam and condensate line. Condensate formed within the dispensing tube drips out the bottom of the dispensing tube and through an aperture at the bottom of the reversing tube, the condensate effectively sealing the bottom of the reversing tube to steam. The condensate purge system includes a back pressure and constant bleed valve having its intake connected to the autoclave steam and condensate line, its outlet connected to a discharge line, and an actuatable by-pass purge valve connected from an internal point in the bleed valve to the discharge line. The purge valve is controllably actuated to effectively drain the bleed valve to prevent the back build up of condensate in the system without interfering with the sterilization operation.

9 Claims, 8 Drawing Figures

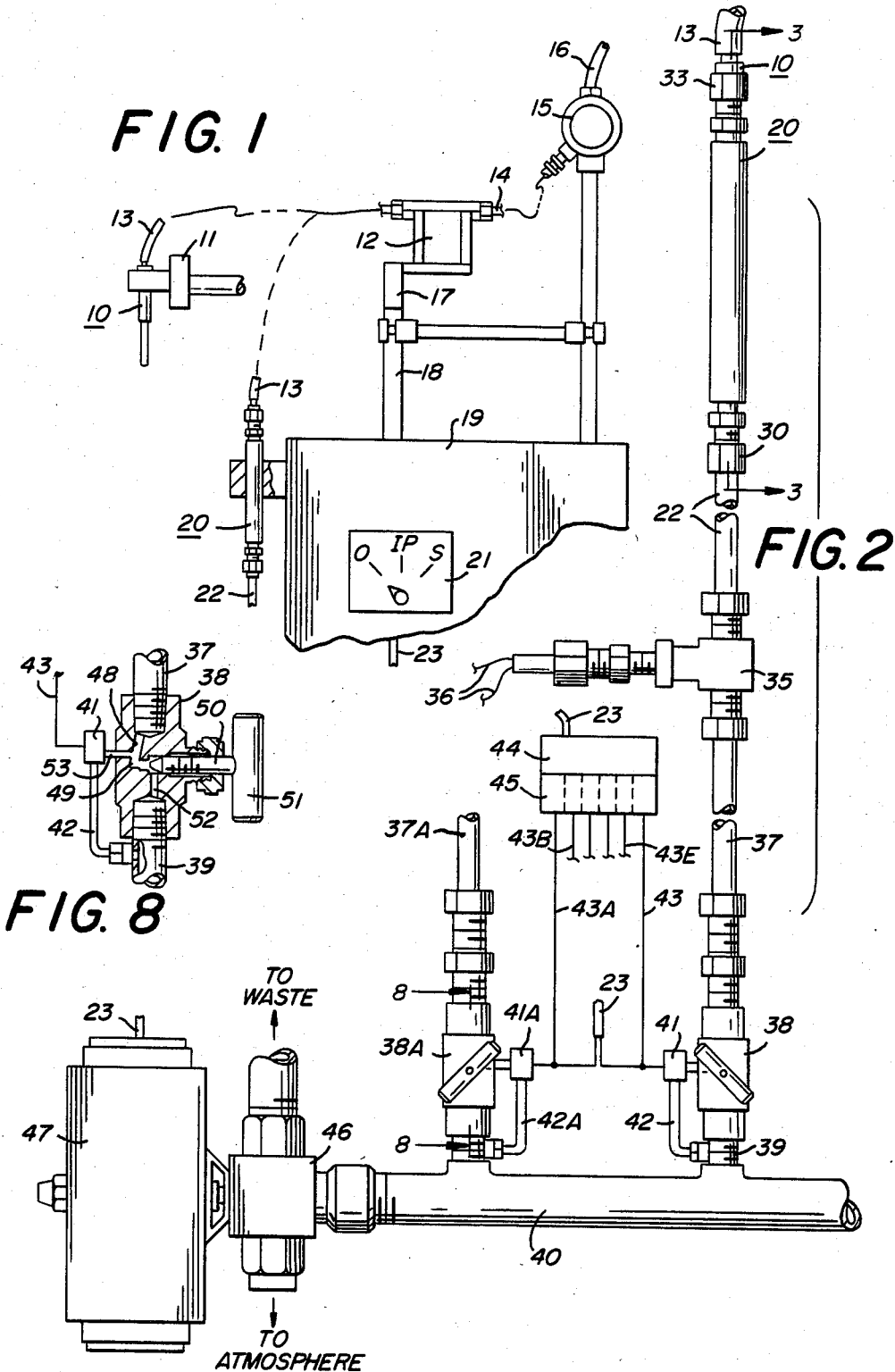

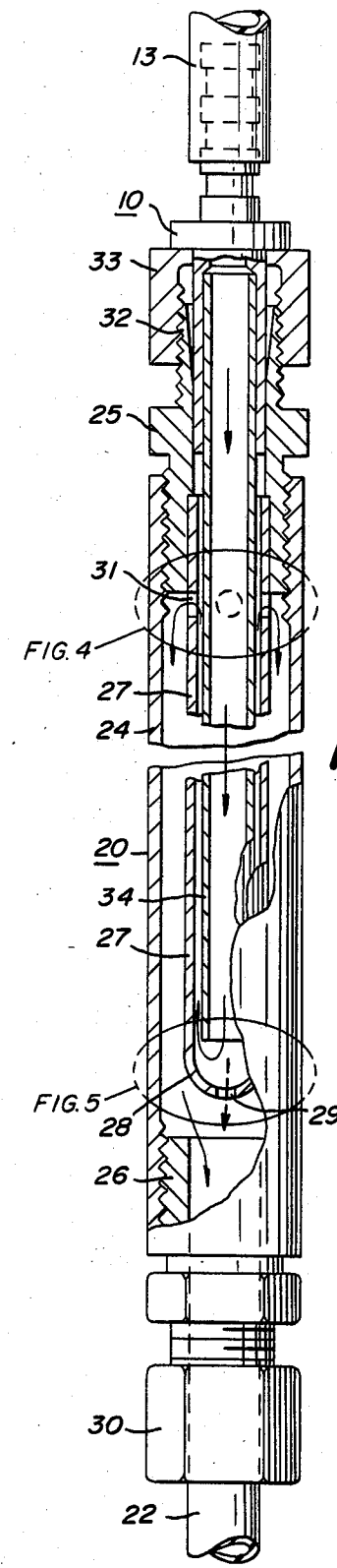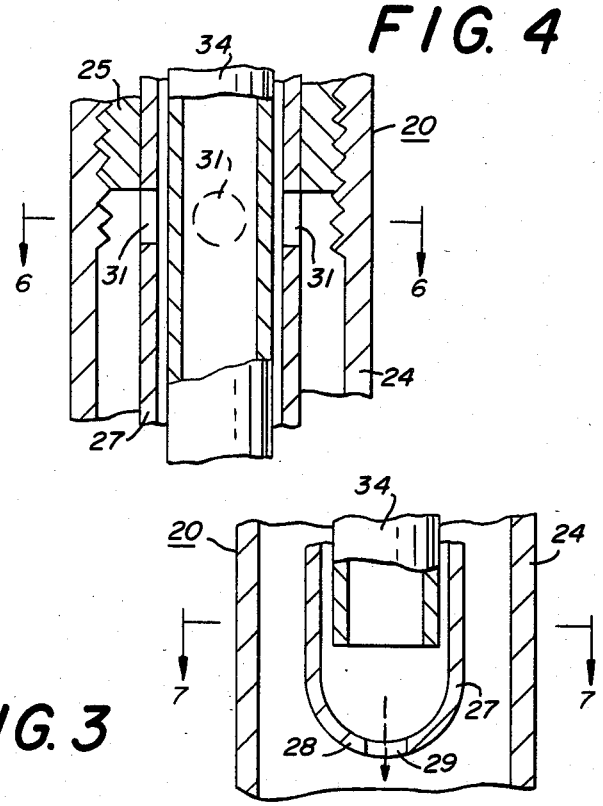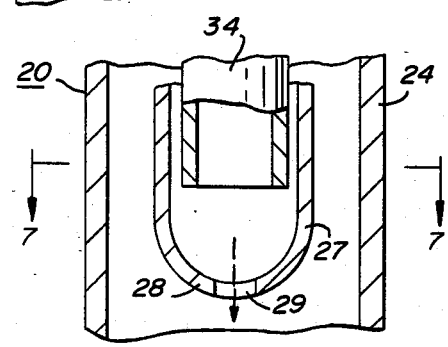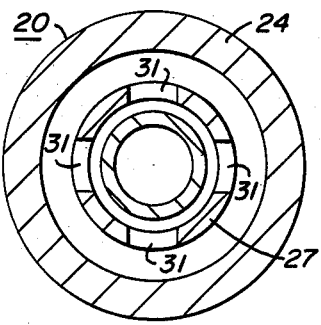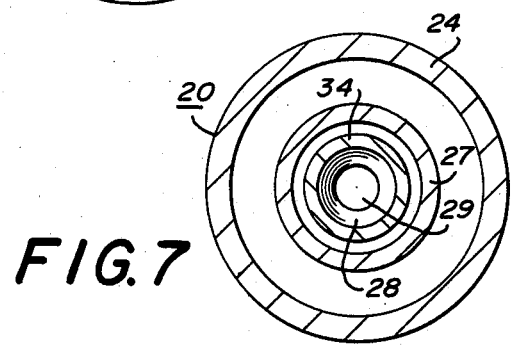

STERILIZATION SYSTEM

This invention relates generally to high speed liquid filling machines, and more particularly relates to a method of and apparatus for sterilizing such machines without disassembly and reassembly, to thereby effect substantial cost savings and insure sterility.

Past practice in high speed filling machines, particularly involving applications where sterilization is required such as in the pharmaceutical industries, required that the machine be shut down and that the components through which the medium to be filled flowed be disassembled and sterilized, and after sterilization be reassembled again. A serious problem with that process is that after sterilization the reassembling of the machine can and often does reintroduce non-sterile conditions. An important aspect of the present invention is that the prior process is modified so that the machine does not have to be disassembled and reassembled. It is sterilized in place without disconnection, and there is no possibility that after the sterilization process has taken place any contaminants can be reintroduced into the system. In the system according to the invention, sterilization is carried out in place by a sterilizing medium of pure saturated steam at 250° F. (or 121° C.).

Basically, the system operates by first closing off the normal functioning of the machine. In the system to be illustrated and described the sterilizing steam is introduced into the product dispensing manifold, and this can be done through the product supply line with the product supply line being at that point disconnected from the product source. Typically that is done by valving off the product supply and then disconnecting the product supply line from the supply source and connecting it to the sterilizing steam source. Alternatively, the sterilization process can be carried back as far into the system as is desired. For example, if the product supply tank has been emptied, the steam can be introduced at some earlier point to clean out or sterilize the product supply tank itself and/or any portion of the line between the tank and product dispensing manifold.

A very large time saving and/or dollar saving is effected by using the system according to the invention. For example, the entire sterilization process can be carried out within an hour and a half and the machine can be back on line and in operation. The alternative method of taking the dispensing heads apart, autoclaving them and then reassembling them requires substantially longer times. For example, it takes an hour for the autoclaving sterilization process, and approximately forty-five minutes per head for disassembly, cleaning and reassembly. In a typical twenty head machine, this would require fifteen man hours of labor for disassembly, cleaning and reassembling the heads, whereas in the system according to the invention, since none of that is required, the entire set-up process takes fifteen minutes irrespective of how many heads there are in the machine. The time savings are therefore substantial.

The only alternative to this would be for the operator to have duplicate machinery so that when one piece of machinery is taken off line the other one can be put on line, and the cleaning and sterilizing process carried out while the second machine is operating. This obviously is hugely expensive, and where a large number of machines are being run in a system would be economically prohibitive. This alternative also results in very large down times for half of the machinery because half of it is being operated and half of it is not being operated because it is being cleaned, so that there is no way to avoid this tremendous financial outlay. Accordingly, the advantages of the system are really two-fold. One of the major advantages is in not having a recontamination problem after sterilization of the machine, and the second large advantage is the economic one in which very substantial monetary savings are effected.

Accordingly, a primary object of the invention is to provide a novel method of and apparatus for sterilization of product filling machinery which eliminates disassembly and reassembly of the machinery and thereby eliminates the possibility of recontamination after sterilization and during reassembly.

Another object of the invention is to provide a novel method of and apparatus for sterilization of product filling machinery as aforesaid which effects substantial monetary savings by drastically reducing the time necessary to carry out a sterilization cycle.

A further object of the invention is to provide a novel method and apparatus as aforesaid utilizing steam sterilization which incorporates a novel steam condensate purge system and a novel autoclave structure.

The foregoing and other objects of the invention will appear more fully hereinafter from a study of the following description and the appended drawings, wherein:

FIG. 1 is a diagrammatic view of a portion of the system according to the invention;

FIG. 2 is a diagrammatic view of another portion of the system according to the invention showing the novel condensate purge system;

FIG. 3 is an enlarged vertical cross section through one of the novel autoclaves as would be seen when viewed along the lines 3—3 of FIG. 2;

FIG. 4 is an enlarged view of the autoclave region shown in the identified phantom circle on FIG. 3;

FIG. 5 is an enlarged view of the autoclave region shown in the identified phantom circle on FIG. 3;

FIG. 6 is a cross section through the autoclave structure as would be seen when viewed along the lines 6—6 of FIG. 4;

FIG. 7 is a cross section through the autoclave structure as would be seen when viewed along the lines 7—7 of FIG. 5; and FIG. 8 is a vertical cross section through a condensate purge valve as would be seen when viewed along the lines 8—8 of FIG. 2.

In the several figures, like elements are denoted by like reference characters.

FIG. 1 shows a part of a filling machine in diagrammatic form including one of the dispensing nozzles 10 held in its reciprocable frame 11 and connected to an air actuatable filling head 12 by a flexible tube 13, the filling head 12 being connected by flexible tubing 14 to a product manifold 15 which latter is connected to a source of product supply by tubing 16. The filling heads 12, of which there normally are a number, are connected to an air manifold 17 which is fed from an air tube 18 that transmits pressurized air to the manifold under control of apparatus contained in the base cabinet 19. Supported from the base cabinet 19 are a plurality of autoclaves 20, one of which is shown, and a three position control switch 21 which is used to control the sterilization system. A steam and condensate line 22 extends from the lower end of the autoclave 20, and a control line 23 extends from the switch 21.

The autoclave 20, as best seen in FIGS. 3 to 7, is formed with an elongated hollow cylindrical shell 24 within which are threadedly secured at the upper and lower ends respectively, a hollow open ended plug 25 and a hollow open ended fitting 26. The plug 25 has peripherally secured to the lower end of its interior open end the upper end of a reversing tube 27, which latter extends downward within the shell 24 to a bottom end 28 which terminates somewhat above the upper end of fitting 26. The very bottom of the reversing tube 27 is provided with an aperture 29 through which steam condensate can drip through the bottom fitting 26 into the steam and condensate line 22 which is secured to the bottom fitting by a compression fitting 30. The sidewall of the upper end of the reversing tube 27 is also apertured immediately below the lower end of the plug 25, as shown at 31. The upper end of plug 25 is formed as an externally threaded compression sleeve 32 upon which is threaded a compression nut 33.

Disposable within the autoclave 20 is the dispensing tube 34 of the nozzle 10 with the upper end of the dispensing tube peripherally sealed and locked within the plug 25 by the compression sleeve 32 and nut 33 and with its outside surface spaced away from the inside surface of the reversing tube 27. As best seen in FIG. 3, the flow path of the sterilizing steam is shown by the solid arrows and follows a path downward through flexible tubing 13 into the top of the dispensing tube 34, downward through the inside of the dispensing tube to its open ended bottom where it reverses and flows upward between the inside face of the reversing tube 27 and the outside face of the dispensing tube 34 to the series of holes 31 through the sidewall of the reversing tube 27 at the elevation immediately below the plug 25. The steam then comes out through the holes 31 and goes down between the outside face of the reversing tube 27 and the inside face of the autoclave shell 24, thereafter passing down into the steam and condensate line 22.

Any condensate which is formed within the dispensing tube 34 as the steam travels downward drips out the bottom of the dispensing tube and through the aperture 29 at the bottom of the reversing tube 27. The aperture 29 is such in size that while no condensation build-up can occur inside the reversing tube 27, it is possible for the condensate to effectively seal the bottom of the reversing tube so that the steam coming out of the bottom of the dispensing tube 34 will reverse flow upward between the dispensing tube and the reversing tube as previously described.

As best seen in FIG. 2 the steam and condensate line 22 connects to a temperature sensing thermocouple 35 which senses the sterilizing temperature and generates electrical signals at leads 36 which correspond to the temperature. The leads 36 are returned inside the base cabinet 19 to actuate a temperature indicator and can also be used to activate automatically sequencing control equipment if desired. The steam and condensate continue past the thermocouple 35 to a steam and condensate line 37 which discharges into the intake end of a back pressure and constant bleed valve 38 which is shown in detail in FIG. 8 to be subsequently described. The discharge end of valve 38 is connected by a discharge line 39 to a condensate manifold 40.

Connected to the valve body is the intake port of an impulse purge valve 41 which has its discharge port connected by a line 42 to the discharge line 39. To the condensate manifold 40 are also connected the discharge ends of all of the other bleed valves in the sterilizing system which receive steam and condensate from other autoclaves, one such other valve being illustrated as 38A. The purge valve 41 is actuated and deactuated during sterilization via a control line 43 by a repeat cycle timer 44 under the control of a step programmer 45, all of the other purge valves, such as 41A, being similarly controlled via control lines 43A through 43E. The cycle timer 44 could typically be an ATC series 342 timer, and the step programmer could be an ATC Model 1800. The condensate manifold has its outlet connected to a three way valve 46 which is actuated by actuator 47 so that the manifold is connected to atmosphere when the sterilization system is not operating and is connected to a waste line when the sterilization system is in operation. Control of the valve actuator 47, timer 44, programmer 45, and purge valves 41 during the Initial Purge operation, is effected from the base cabinet switch 21 through control line 23.

Details of the valve 38 and purge system are shown in FIG. 8 to which reference should be made. The intake of the valve 38 empties into a small vertical passage 48 which connects at its bottom to a horizontal passage 49 into which is threadedly engaged a valve stem 50 which may be advanced and retracted by the valve handle 51 to variably open and close the passage 49 to control the size of the opening between the passage 49 and the vertical exit passage 52 and thereby control the back pressure in the steam line. The intake vertical passage 48 also connects, near its junction with the horizontal passage 49, to a horizontal passage 53 which couples to the intake port of purge valve 41, the discharge port being connected, as previously described, to the discharge line 39 by the line 42.

The sequence of events that takes place in carrying out the steam sterilization according to the invention is as follows. First, the supply of product is cut off from the product manifold 15 in whatever manner is convenient, as for example by valving. Next, the dispensing nozzles 10 are each removed from their operatively held position for dispensing product and are each inserted into and secured within a separate autoclave 20 as previously described. In FIG. 1 only one such nozzle is illustrated, but as schematically shown in FIG. 2 this process is carried out for all of the nozzles in the entire apparatus. Assuming that sterilizing steam is available at this point, the switch 21 on the base cabinet 19 is moved from its "Off" (O) position to the Initial Purge (IP) position. This causes the three-way valve to change its position so that the condensate manifold which had been connected to atmosphere is now connected to the waste line.

Actuating pulses from control line 23 are simultaneously routed to all of the impulse purge valves 41, 41A and so forth, so that all of the valves are opened simultaneously to by-pass each of the constant bleed valves 38. This allows steam to flow through the entire system rapidly to quickly purge out all of the air and non-condensable gases that are in the system. At this initial point in the sterilization cycle any steam temperature drop which occurs is not critically important since it will be followed up with sterilizing temperatures. This initial purge condition is maintained until the thermocouples 35 sensing the temperatures in the autoclaves 20 indicate that the system is coming up to temperature. The actual time that this requires is a function of the size of the system, that is, how many heads are being autoclaved, and whether just the dispensing nozzles are being sterilized or whether some larger part of the system which has more mass to it is being sterilized, such as the product holding tank. In any event this allows the system to come up to temperature much more rapidly than if the steam had to flow through the back pressure and constant bleed valves 38.

It is desired that those valves 38 be initially adjusted and that they not have to be thereafter frequently readjusted. The adjustment for back pressure is such that the valves 38 will not be in maximum flow condition during normal sterilization cycle, and therefore the impulse purge valves being all simultaneously opened allows a much faster steam flow through the system, and consequently a more rapid rise in temperature within the system so that the sterilization process can be started sooner.

When the initial purge has been completed the switch 21 on the base cabinet 19 is moved from the "IP" position to the "S" or sterilize position. This activates the cycle timer 44 and step programmer 45 via control line 23 for carrying out a sequentially controlled purge process and discontinues the simultaneous activation of the purge valves. The steaming process goes on continuously during the sterilization time, and all of the nozzles of the system are simultaneously subjected to the sterilizing steam on a continuous basis. While this continuous steaming process is going on there is also a cyclic condensate purge process that is carried out, and this purge process is carried out nozzle by nozzle in a timed sequence. The sequence is such that the purge for each nozzle takes place for a selected time interval of perhaps up to two seconds in length. The reason for purging on a sequential basis is that if purging of all of the autoclaves were done simultaneously the steam source would be depleted and would result in a temperature drop below the required sterilization temperature of 250° F. In order to avoid this, the purge operation is carried out sequentially so that only one autoclave at a time is being purged, not the entire group, which could be as many as thirty-two or more separate autoclaves.

The purpose of the purge operation is best understood by reference again to FIG. 8. From that showing it will be clear that condensate which may puddle up in the internal passages of the valve cannot bleed through to the discharge condensate manifold 40 as rapidly as the steam or gas phase can, and as a consequence condensate can start to build up in that valve and back-up into the autoclave, thereby interfering with the steam sterilization process going on therein. For purposes of eliminating this problem the impulse purge valves 41 are provided. By means of the purge valve actuation for a short time period whatever condensate may have collected at the bleed valve passage 49 is rapidly bypassed to the larger passageway 42 around the valve structure and into the condensate manifold line. This eliminates the problem of condensate build-up into the autoclave structures.

The impulse purge valves 41 are controlled by timing pulses from the cycle timer 44 which actuate the purge valves to open under control of the step programmer 45. The cycle timer 44 produces the selectable length of actuating pulse that is desired, and this pulse, which is being repeatedly generated, is distributed out to each of the impulse purge valves in a timed sequence as controlled by the step programmer 45. This sequence is continuous during the course of the entire sterilization process. That is, while the steam sterilization may be going on for as long as forty-five minutes to an hour, the impulse purge valves are being operated in sequence for timed intervals of up to two seconds each, and this sequence is continuously repeating itself throughout the course of the sterilization process.

Having now described the invention in connection with particularly illustrated embodiments thereof, it will be appreciated that variations and modifications of the invention may now naturally occur from time to time to those persons normally skilled in the art without departing from the essential spirit or scope of the invention, and accordingly it is intended to claim the same broadly as well as specifically as indicated by the appended claims.

What is claimed to be new and useful is:

1. A filling machine including sterilizing apparatus, comprising in combination:
    (a) a filling machine of the type having at least one dispensing nozzle having an inlet end normally coupled to a source of product to be dispensed and having an outlet end through which product is discharged,
    (b) autoclave means comprising at least one auto clave having an insert opening into which the dispensing nozzle is insertable, sealing means for sealing the autoclave means insert opening with the nozzle therewithin, and a discharge opening,
    (c) means for decoupling the nozzle from a source of product to be dispensed and for coupling the nozzle inlet end to a source of fluent sterilizing medium,
    (d) pressure regulating means having an inlet coupled to the discharge opening of said at least one auto clave, an outlet coupled to a discharge line, and adjustable means for controlling the rate of flow of a fluent sterilizing medium through said pressure regulating means from said inlet to said outlet and thereby adjusting the back pressure at the inlet of said pressure regulating means,
    (e) selectively actuatable pressure regulating means by-pass means effective when actuated to by-pass said adjustable means for controlling the rate of flow of a fluent sterilizing medium to thereby reduce the back pressure at the inlet of the pressure regulating means, and
    (f) control means for actuating said by-pass means.

2. Apparatus as described in claim 1 wherein:
    (a) said autoclave means comprises a plurality of separate autoclaves as described and said filling machine comprises a plurality of said nozzles wherein each of said autoclaves receives a different dispensing nozzle as described,
    (b) said pressure regulating means comprises a plurality of separate pressure regulating means as described and each of which is coupled to a different one of said separate autoclaves, and
    (c) said by-pass means comprises a plurality of separate by-pass means as described and each of which is associated with a different one of said separate pressure regulating means.

3. Apparatus as described in claim 2 wherein said control means includes means for simultaneously actuating and deactuating all of said pressure regulating means by-pass means.

4. Apparatus as described in claim 2 wherein said control means comprises repeat cycle timing pulse generating means effective to generate a continuous train of timing pulses which are each effective to actuate said by-pass means when coupled thereto, and step programmer means coupled to said timing pulse generating means to receive timing pulses therefrom, said step programmer means being also coupled to all of said by-pass means and being effective to cyclically couple timing pulses from said pulse generating means sequentially to all of said by-pass means, whereby each said pressure regulating means is sequentially and cyclically by-passed during the sterilization process under control of said control means.

5. A filling machine including sterilizing apparatus, comprising in combination:
   (a) a filling machine of the type having at least one dispensing nozzle having an inlet end normally coupled to a source of product to be dispensed and having an outlet end through which product is discharged,
   (b) autoclave means having an insert opening into which the dispensing nozzle is insertable, sealing means for sealing the autoclave means insert opening with the nozzle therewithin, and a discharge opening, said auto clave means further comprising
      (1) a first chamber into which said dispensing nozzle is insertable, said first chamber having an inside surface and an outside surface and being sized so that said nozzle outlet end and the major part of the outside surface of said nozzle is out of contact with the inside surface of said first chamber, and said first chamber having a first exit opening therefrom at a location remote from said nozzle outlet end in the direction of said nozzle inlet end,
      (2) a second chamber within which said first chamber is disposed with said first chamber first exit opening located proximate to one end of said second chamber, and said autoclave discharge opening exiting from said second chamber whereby, fluent sterilizing medium follows a flow path from the said nozzle inlet end through the inside of the nozzle to the outlet end, and reverses its flow to flow around the major part of the outside surface of said nozzle before passing from said first chamber through said first exist opening into said second chamber and then exiting from said second chamber through said autoclave discharge opening,
   (c) means for decoupling the nozzle from a source of product to be dispensed and for coupling the nozzle inlet end to a source of fluent sterilizing medium,
   (d) pressure regulating means having an inlet coupled to the autoclave means discharge opening, an outlet coupled to a discharge line, and adjustable means for controlling the rate of flow of a fluent sterilizing medium through said pressure regulating means from said inlet to said outlet and thereby adjusting the back pressure at the inlet of said pressure regulating means,
   (e) selectively actuatable pressure regulating means bypass means effective when actuated to by-pass said adjustable means for controlling the rate of flow of a fluent sterilizing medium to thereby reduce the back pressure at the inlet of said pressure regulating means, and
   (f) control means for actuating said by-pass means.

6. Apparatus as described in claim 5 wherein said first chamber is provided with a second exit opening therefrom proximate to the position of the dispensing nozzle outlet end when the nozzle is inserted in the said first chamber, said second exit opening providing a second path to said autoclave discharge opening.

7. Apparatus as described in claim 5 wherein the fluent sterilizing medium is pure saturated steam, and wherein said first chamber is provided with a second exit opening therefrom proximate to the position of the dispensing nozzle outlet end when the nozzle is inserted in the said first chamber, said second exit opening providing a second path to said autoclave discharge opening for steam which has condensed within said first chamber, the size of said second exit opening being such that condensate blocks the opening to prevent exit therethrough of vapor phase steam and causes the latter to first exit said first chamber through the said exit opening into said second chamber.

8. Apparatus as described in claim 5, 6 or 7 wherein:
   (a) said dispensing nozzle is in the form of an elongated open ended tube,
   (b) said first chamber is in the form of an elongated tube of larger diameter than and slightly longer than said dispensing nozzle tube, and
   (c) said second chamber is in the form of a hollow cylinder of larger diameter than and longer than said first chamber, said autoclave discharge oepning being at the end of said second chamber at the opposite end to the end where said first exit opening of said first chamber is located.

9. A fluent medium flow control system comprising in combination,
   (a) pressure regulating means having an inlet to receive a fluent medium, an outlet to discharge a fluent medium, and adjustable means for controlling the rate of flow of a fluent medium through said pressure regulating means from said inlet to said outlet to thereby adjust the back pressure at the inlet,
   (b) selectively actuatable pressure regulating means by-pass means coupled to said inlet and to said outlet of said pressure regulating means, and effective when actuated to by-pass said adjustable means for controlling the rate of flow of a fluent medium and thereby reduce the back pressure at the inlet, and
   (c) control means for actuating said by-pass means, said pressure regulating means and said by-pass means each being plural, and said control means comprising repeat cycle timing pulse generating means effective to generate a continuous train of timing pulses which are each effective to actuate said by-pass means when coupled thereto, and step programmer means coupled to said timing pulse generating means to receive timing pulses therefrom, said step programmer means being also coupled to all of said by-pass means and being effective to cyclically couple timing pulses from said pulse generating means sequentially to all of said by-pass means, whereby each said pressure regulating means is sequentially and cyclically by-passed under control of said control means.

* * * * *